United States Patent [19]

Uram

[11] Patent Number: 5,121,740
[45] Date of Patent: Jun. 16, 1992

[54] LASER VIDEO ENDOSCOPE

[76] Inventor: Martin Uram, 39 Sycamore Ave., Little Silver, N.J. 07739

[21] Appl. No.: 737,054

[22] Filed: Jul. 29, 1991

Related U.S. Application Data

[63] Continuation-in-part of Ser. No. 696,117, May 6, 1991, abandoned.

[51] Int. Cl.$^5$ .................... A61B 1/06; A61B 17/32
[52] U.S. Cl. ................................ 128/6; 128/11
[58] Field of Search ...................... 128/6, 7, 11, 4

[56] References Cited

U.S. PATENT DOCUMENTS

| | | | |
|---|---|---|---|
| 3,858,577 | 1/1975 | Bass et al. | 128/8 |
| 4,072,147 | 2/1978 | Hett | 128/6 |
| 4,170,997 | 10/1979 | Pinnow et al. | |
| 4,207,874 | 6/1980 | Choy | 128/6 |
| 4,448,188 | 5/1984 | Loeb | 128/6 |
| 4,589,404 | 5/1986 | Barath et al. | 128/6 |
| 4,604,992 | 8/1986 | Sato | 128/6 |
| 4,607,622 | 8/1986 | Fritch et al. | 128/6 |
| 4,624,243 | 11/1986 | Lowery et al. | 128/6 |
| 4,697,210 | 9/1987 | Toyota et al. | 128/6 |
| 4,700,694 | 10/1987 | Shishido | 128/6 |
| 4,754,328 | 6/1988 | Barath et al. | 128/6 |
| 4,765,313 | 8/1988 | Kumakura | 128/6 |
| 4,790,295 | 12/1988 | Tashiro | 128/6 |
| 4,807,598 | 2/1989 | Hasegawa | 128/6 |
| 4,830,460 | 5/1989 | Goldenberg | 128/6 |
| 4,834,070 | 5/1989 | Saitou | 128/6 |
| 4,856,495 | 8/1989 | Tohjoh et al. | 128/6 |
| 4,867,137 | 9/1989 | Takahashi | 128/6 |
| 4,896,941 | 1/1990 | Hayashi et al. | 128/6 |
| 4,916,534 | 4/1990 | Takahashi et al. | 128/6 |
| 4,928,695 | 5/1990 | Goldman et al. | 128/6 |
| 4,948,894 | 8/1990 | Kawashima | 128/6 |
| 4,965,960 | 10/1990 | Takami | 128/6 |
| 4,984,563 | 1/1991 | Renaud | 128/6 |

Primary Examiner—Paul J. Hirsch
Attorney, Agent, or Firm—McAulay Fisher Nissen Goldberg & Kiel

[57] ABSTRACT

A surgical endoscope particularly adapted for use in ophthalmological surgery includes a probe connected distally of a hand piece. Within the probe, there are three sets of optical fibers. The first set of optical fibers are five-hundred thirty micron fibers which constitute an illumination zone for illuminating the tissue to be operated on. An image guide has 3,000 three micron fibers, providing a 3,000 pixel image of the tissue. The distal end of the image guide has an objective lens bonded to it which preferably has a one mm to infinity depth of field. A laser fiber with an active diameter of two hundred microns provides pulses of laser energy to the tissue illuminated by the illumination fibers and imaged by the image fibers.

6 Claims, 1 Drawing Sheet

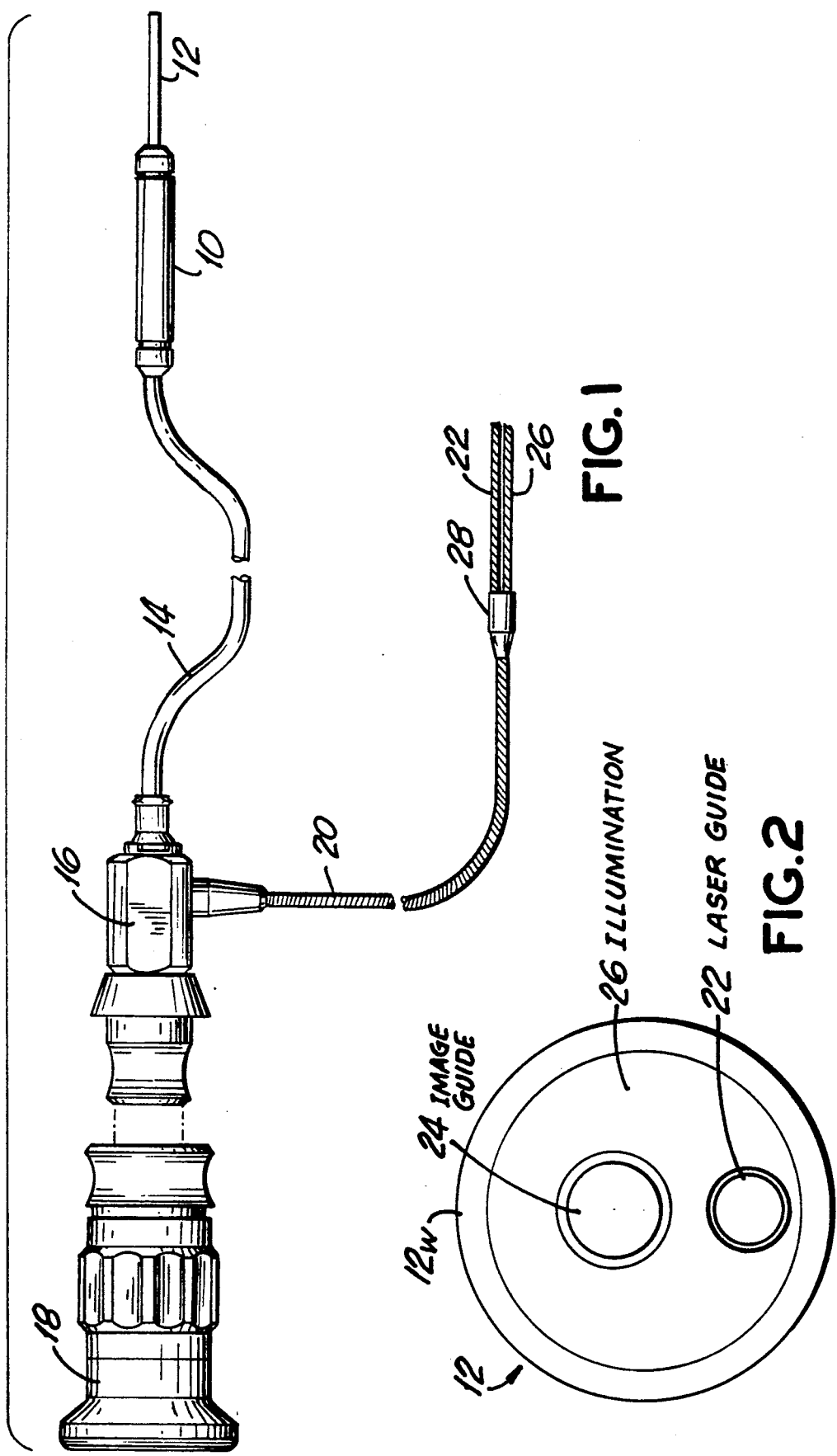

LASER VIDEO ENDOSCOPE

REFERENCE TO RELATED APPLICATIONS

This application is a continuation-in-part of applicant's patent application Ser. No. 07/696,117 filed on May 6, 1991 and entitled: Laser Video Endoscope now abandoned.

This invention relates in general to a small diameter endoscope used for medical purposes and more particularly to one in which illumination, viewing and laser operating functions are performed within a single relatively small diameter endoscope.

The endoscope of this invention is designed particularly for use in certain ophthalmological operations and thus the disclosure herein will relate to such an embodiment.

It is known to apply laser energy, and other types of energy, both directly and indirectly to various parts of the eye in order to effect surgery. For example, it is known to laser the peripheral retina for treatment of retina detachment. It is also known, in appropriate circumstances, to directly laser the ciliary processes as one of the treatments for glaucoma. Because of the difficulty of applying laser energy directly to the ciliary processes, the standard technique for disabling ciliary processes has been a cryogenic technique. This cryogenic technique involves applying a freezing probe on the external surface of the eye overlying the ciliary processes on the inside of the eye. The ciliary processes are then frozen and thawed. This destroys the ciliary processes and thus reduces the aqueous output that builds up pressure. This process is fairly brutal in its immediate effect on the eye. Vision can be frequently lost. It is extremely difficult to titrate. There is a risk of shrinkage and atrophy of the eye due to overtreatment.

It is clearly preferable to apply a destructive element, such as a laser, directly to the ciliary processes. This has been done only where it is accompanied by a vitrectomy and lensectomy operation. That is only desirable or feasible in a very small number of cases.

It is a specific purpose of this invention to provide an intraocular endoscope that will be useful in photocoagulating any internal area of the eye including, most importantly, the pars plana region, the ciliary processes and the posterior aspect of the iris.

A further and related purpose of this invention is to allow more complete photocoagulation of the peripheral retina in the treatment of complicated retina detachment or proliferative retinopathies such as in diabetes mellitus.

It is a further and a related purpose of this invention to provide the above functions in a product which is relatively easy for a surgeon to use so that the operations involved can be precisely determined and can be more complete than is presently feasible.

Another related purpose of the invention is to provide an endoscope product that performs the above functions at a cost which makes it feasible for appropriate ocular surgery to be undertaken on a relatively widespread basis by a relatively large number of ophthalmologists.

BRIEF DESCRIPTION

In brief, this invention involves a fiber optic endoscope having a probe supported by a handpiece. The hand piece is connected through a relatively long flexible lead to a laser energy source, a source of illumination and an optical eye piece. The flexible lead, hand piece and probe all contain a laser optical fiber, an optical fiber image guide and an optical fiber illumination zone. The image guide fibers and the laser fiber are surrounded by the set of illumination fibers.

The laser fiber is a monofilament fiber that provides the required pulses of laser energy to effect operation. In one embodiment, it has a diameter of approximately 0.2 mm. The image guide is a set of high resolution fused quartz image fibers that provide a 3,000 pixel image, each pixel having a three micron diameter. The image guide has a diameter of 0.25 mm. An objective lens having a depth of field from down to about one mm is bonded to the distal end of the image guide.

This image guide and laser fiber are embedded within a set of fibers which carry illumination toward the distal end of the probe.

Light transmitted down the illumination fibers emerges at the distal end of the probe to provide illumination at the area of operation. The image of at least part of the area illuminated is transmitted back through the set of fibers that constitute the image guide to be viewed by the surgeon at an eyepiece or by video or still photography. With the image in view and the probe in position, the surgeon can then control the transmission of laser energy, typically pulses of laser energy, through the monofilament laser fiber to the zone of the operation.

BRIEF DESCRIPTION OF THE FIGURES

FIG. 1 is a mechanical schematic longitudinal view of an embodiment to this invention.

FIG. 2 is a cross-sectional view at the tip of the probe illustrating the relative deployment of the monofilament laser fiber 22, the 3,000 pixel image guide 24 and the multi-fiber illumination zone 26.

DESCRIPTION OF THE PREFERRED EMBODIMENTS

As shown in the Figures, one embodiment of the endoscope of this invention has a hand piece 10 and a probe 12, which are connected through a first flexible cable 14 to a connector 16. An eyepiece 18 is optically coupled to the connector 16 for viewing purposes. A second flexible cable 20 extends out of the side of the connector 16.

Within the probe 12, the hand piece 10 and the first flexible cable 14 there is deployed three separate sets of optical fibers that perform three separate functions. These are shown in the cross-sectional view of FIG. 2. This cross-sectional view is one taken at the tip of the probe 12. Within the probe 12 there is a monofilament laser fiber 22, an image guide 24 and an illumination zone 26. The laser fiber 22 is a monofilament optical fiber that delivers the laser energy at the tip of the probe 12 for performing operations. The image guide 24 is a set of high resolution fused quartz image fibers that provide a 3,000 pixel image, each pixel having a 3 micron diameter. The illumination zone 26 is composed of a large number of fibers which carry illumination toward the distal end of the probe 12. All of these optical fiber elements are quartz fibers.

In operation, light is transmitted down the illumination zone 22 to emerge at the distal end of the probe 12 to provide illumination at the area of operation. The image of at least part of the area illuminated is transmitted back through the image guide 24 to be viewed by the surgeon at the eyepiece 18. With the image in view and the probe 12 in position, the surgeon can then control the transmission of laser energy (usually pulses of laser energy) through the laser fiber 22 to the zone of the operation.

Because of the small diameter of the probe 12 (under one mm) this endoscope can be used for operations in areas (particularly for eye operations) where a combined viewing and operating endoscope was not hitherto possible.

At the juncture 16, the imaging set of optical fibers 16 is separated from the other two sets of optical fibers so that only the laser fiber 22 and illumination fibers 26 extend down through the tube 20. As indicated at the juncture 28, these two sets of fibers 22 and 26 are further separated to be appropriately connected to a source of laser energy for the optical fiber set 22 and to a source of light for the set of fibers that constitute the illumination zone 26.

It should be noted that the image provided by the image guide 24 can be applied to an eye piece 18 or can be displayed by a video or can be applied to create a still photograph. Indeed, it is anticipated that a video display might be preferable to facilitate the surgeon's positioning in order to manipulate the probe 12 properly.

In one embodiment that has been tested, the probe 12 has an outer diameter of 950 microns with a steel side wall 12w of 75 microns and thus an inner diameter of 800 microns.

In that embodiment, the laser fiber 22 is a monofilament fiber with an active diameter of 200 microns. The cladding and protective buffer layer to prevent mechanical abrasion of the cladding brings the diameter to 250 microns.

In that embodiment, the illumination zone 26 has 500 optical fibers, each fiber having a diameter of 30 microns including cladding. The optical fibers in the illumination zone 26 are strung randomly down the length of the instrument and are potted into place only at the tip of the operating probe 12.

In that embodiment, the image guide 24 has 3,000 quartz fibers, each only 3 microns in diameter including cladding. The fibers are fused to provide a single convenient to handle guide with 3,000 pixels. The guide wall is a thin black protective PVC sleeve 45 microns thick. This image guide 24 has a 250 micron diameter which with the PVC sleeve becomes 340 microns.

In that embodiment, the probe 12 is 30 mm long, the hand piece 10 in 40 mm long and the cable 14 is 410 mm long.

In one preferred embodiment, which has been tested, an objective lens is bonded to the distal end of the image guide 24 fibers and provides a depth of field from one mm to infinity with a field of view of 70 degrees. A depth of field that can go down to as little as one mm is important to aid the surgeon to position the end of the laser guide 22 as close as one mm from the tissue on which the laser energy is to be delivered. It is important to have the distal end of the laser guide and the distal end of the image guide at the same plane. The reason relates to a combination of the fact that (a) with a single probe there is no stereopsis, (b) the need to deliver the laser energy as close as possible to the tissue being worked on, and (c) the importance of avoiding tissue puncture or contact.

The lens is a triple lens of a known type. It is bonded to the image guide 24 prior to assembling the image guide 24 in the illumination zone so that the distal surface of the lens (2 mm which is one embodiment) is flush with the distal end of the probe.

Very minute working distances have to be traversed by means of the operator's hand movements. These minute working distances are in part required by the fact that the laser energy should be delivered only to a specific small zone of tissue which is to be operated on. This requires that the distal end of the laser guide be brought as close as possible to the tissue. A distance of one mm is desirable. But it is essential that the surgeon be able to view the tissue being operated on at the one mm distance in order to avoid having the probe contact, damage or puncture the tissue.

In known types of operations where an operating microscope is employed, an image is provided with a degree of stereopsis which aids the surgeon in moving toward the tissue. But with a probe that incorporates both imaging and laser delivery, stereopsis is not available and it is essential that the laser guide not extend past the image guide in order to make sure that tissue damage is avoided.

Having a wide field of view, such as 70 degrees, is useful to enable the surgeon to locate the various tissue zone areas which have to be operated on and to which energy has to be delivered.

As is known in the art, the particular laser guide optical material is selected as a function of the frequency of the laser light pulses which are to be transmitted by the guide. In the embodiment tested, the laser used is a diode laser composed of gallium-aluminum-arsenide semi-conducting crystals to provide a wave length of about 810 nano meters (in the range of 780 nm to 850 nm).

The joints 28 and 16 where the different components 22, 24 and 26 of the interior of the probe 12 are brought together are fabricated as junctions by standard techniques known in the art including the use of heat shrink tubing at the connector 28.

The embodiment has the straight probe 12 shown. Applicant believes there may be advantage in a slight curvature to the probe 12 so that the tip of the probe is displaced two to three mm from the axis. This might provide advantage in use of more readily clearing the lens of the eye.

It should be noted that the combination of the illumination zone, the image guide and laser guide within a single probe provides a particularly compact probe for performing these three functions, which because it is compact and circular in cross section requires a minimal incision of the cornea while meeting the objectives of this invention including an ability to access areas such as the ciliary processes which otherwise require the use of multiple instruments.

What I claim is:

1. In a surgical endoscope having a hand piece and a connecting cable attached to the proximal end of the hand piece, the improvement in a small diameter probe comprising:

a rigid tubular sidewall having a circular cross-section, an illumination guide comprising a first set of optical fibers extending longitudinally within said sidewall, an image guide comprising a second set of optical fibers extending longitudinally within said sidewall, an optical laser guide comprising a third set of optical fibers extending longitudinally within said sidewall, said illumination guide, said image guide and said laser guide constituting substantially the only functional components within said tubular sidewall of said probe, said first, second and third sets of optical fibers constituting a combined set of optical fibers having a circular outer diameter, said circular outer diameter being substantially equal to the inner diameter of said tubular sidewall, said image guide and said optical laser guide terminating in substantially the same plane at the distal end of said rigid probe, whereby light applied through said illumination zone will generate an image at the distal end of said rigid probe which can be viewed through said image guide simultaneous with application of laser energy through said laser guide.

2. The endoscope improvement of claim 1 wherein: said optical laser guide is a monofilament laser fiber.

3. The endoscope improvement of claim 2 wherein:
said combined set of optical fibers have an outer diameter no greater than approximately 800 microns,
said image guide is circular in cross-section and has an outer diameter of approximately 250 microns,
said laser guide including cladding has an outer diameter of approximately 250 microns.

4. The endoscope improvement of claim 1 further comprising:
an objective lens bonded to the distal end of said image guide to provide a depth of field ranging between infinity and approximately one millimeter.

5. The endoscope of claim 2 further comprising:
an objective lens bonded to the distal end of said image guide to provide a depth of field ranging between infinity and approximately one millimeter.

6. The endoscope of claim 3 further comprising:
an objective lens bonded to the distal end of said image guide to provide a depth of field ranging between infinity and approximately one millimeter.

* * * * *